United States Patent [19]

Greiff et al.

[11] Patent Number: 4,936,297

[45] Date of Patent: Jun. 26, 1990

[54] DEVICE FOR THE ENRICHMENT OF RESPIRATORY AIR WITH OXYGEN

[75] Inventors: Rudolf Greiff, Badendorf; Wolfgang Rittner, Bad Schwartau, both of Fed. Rep. of Germany

[73] Assignee: Drägerwerk AG, Lübeck, Fed. Rep. of Germany

[21] Appl. No.: 354,495

[22] Filed: May 19, 1989

[30] Foreign Application Priority Data

May 30, 1988 [DE] Fed. Rep. of Germany ....... 3818280

[51] Int. Cl.[5] ............................................. A61M 16/00

[52] U.S. Cl. .......................... 128/203.25; 137/625.29; 251/142

[58] Field of Search ...................... 128/203.25, 204.18, 128/205.11; 137/109-114, 88, 625.28, 625.29, 3; 251/142, 149

[56] References Cited

U.S. PATENT DOCUMENTS 3,669,134 6/1972 Dorbritz ........................ 128/203.25
4,072,148 2/1978 Munson et al. ................ 128/205.11
4,576,159 3/1986 Hahn et al. ..................... 128/203.25
4,602,653 7/1986 Ruiz-Vela et al. ............. 128/205.11

FOREIGN PATENT DOCUMENTS 2133714 8/1984 United Kingdom ........... 128/203.25

*Primary Examiner*—Eugene H. Eickholt
*Attorney, Agent, or Firm*—McGlew & Tuttle

[57] ABSTRACT

A device for the enrichment of respiratory air with oxygen, includes a supply gas to be enriched which is supplied to at least one concentrator and from there to a product gas line in an adjustable concentration of enrichment. The required concentration of enrichment is adjusted speedily and without loss to the changing amount which is used, and as high a concentration of enrichment as possible at an adjustable and low throughput of the concentrator is achieved by use of a partial flow of the supply gas through a throughput-adjustable bypass line. The bypass line bypasses the product gas line and at least one concentrator.

10 Claims, 2 Drawing Sheets

DEVICE FOR THE ENRICHMENT OF RESPIRATORY AIR WITH OXYGEN

FIELD AND BACKGROUND OF THE INVENTION

The invention relates in general to respirators and in particular to a new and useful device for the enrichment of respiratory air with oxygen, wherein the supply gas to be enriched can be supplied to at least one concentrator and from there to a product gas line in an adjustable concentration of enrichment.

For the enrichment of the supply gas, known devices use pressure exchange adsorption beds which are filled with zeolite. However, permeators equipped with an oxygen-permeable membrane can be used also. In the following, these two enrichment units will be referred to as concentrators. They are used in particular to ensure that the oxygen concentration required for the respiratory air supply of flight personnel used at various altitudes. Such a device is known from DE-OS 28 37 281.

In the known device the respiratory air to be enriched with oxygen is led through the concentrator, in which the nitrogen is retained, and the enriched respiratory air is supplied to the user. The concentration of the oxygen permeated depends essentially on the amount of supply gas flowing through it. If the user requires a lower oxygen concentration, the throughput of the concentrator is increased, the excess amount of enriched product gas being collected in a buffer container. If the amount taken from the buffer container falls below the amount delivered by the concentrator, the excess air is released into the surroundings.

As in the known device the concentration of the enrichment of the product gas is determined by the throughput of supply gas through the concentrator, an adjustment of enrichment to the product gas required usually results in an unnecessary loss of product gas.

If during an unexpected decompression in the personnel section the concentration of enrichment, particularly with an oxygen enrichment, has to be increased to the physiologically required parameters. With the known concentrator this can only be effected by reducing the throughput. In this case however, the increase of the oxygen concentration takes place at so large a time constant that a speedy change of the concentration of enrichment can not be realized. Therefore, an additional back-up system is required for the known device, which can deliver respiratory air with an increased oxygen concentration for a short period and at short notice.

SUMMARY OF THE INVENTION

The present invention provides a device for the enrichment of respiratory air so that the required concentration of enrichment can be adapted speedily and without losses to the changing requirements and so that the user can be supplied with an increased concentration of enrichment gas when required.

A partial flow of the supply gas is supplied over a throughput-adjustable bypass line which bypasses the product gas line and also at least one concentrator in order to achieve as high an enrichment as possible at a continuously small throughput of the concentrator.

An advantage achieved by this invention is that the throughput of the concentrator can be adjusted to yield a maximum concentration of enrichment, and a concentration of enrichment exceeding the required parameters is achieved at the product gas line. By feeding non-enriched supply gas into the product gas line and regulating the throughput of the bypass line, the increased concentration of enrichment can be mixed down to the parameter required. By dividing the supply gas into a part flowing through the concentrator and another part circumventing the concentrator by means of the bypass line the desired concentration of enrichment can be adjusted within a wide range without any loss of product gas to the environment.

In the case of an unexpected decompression the throughput of the bypass line only has to be reduced or closed down entirely in order to be able to speedily supply a higher concentration of enrichment in the product gas to the user. An independent back-up system therefore becomes superfluous.

Advantageously a buffer container is attached to the product gas line, which can also be circumvented by the bypass line, and which can be used as a storage container for the product gas having a high concentration of enrichment.

If the concentrator comprises e.g. several pressure exchange adsorption beds or permeators connected in line, it can be advantageous to connect the supply side opening of the bypass line to the connection line between two concentrators. The product gas is then supplied with pre-enriched supply gas. In this case the high concentration of enrichment cannot be diluted down to very low parameters, but the dilution is effected with increased accuracy.

Advantageously the bypass line is connected to a lateral tapping point of the concentrator. The tapping point is arranged rather at the beginning of the adsorption bed or the permeator, so that only little, but nearly dry supply gas is led into the product gas through the bypass line. By this means the condensation of the product gas which is mixed with the supply gas in the downstream lines all the way to the user is avoided and the freezing of moisture at extremely low temperatures of the surroundings is eliminated.

For an automatic control of the proportions of product gas and mixed-in supply gas it is advantageous to provide a detector in the mixed gas line in order to measure a gas-specific parameter, e.g. the concentration of enrichment or the oxygen contents, and to provide it as a set value for a control unit which adjusts a mixing element at the intersection between the product gas line and the bypass line depending on the desired set value.

Advantageously a further branch line is provided on the bypass line, from which dry supply gas can be tapped for the condensation-free washing of humidity-sensitive elements.

Accordingly, it is an object of the invention to provide a device for the enrichment of respiratory air with oxygen which comprises a gas supply line with an oxygen enrichment device in the supply line having a product gas line discharge and which includes a mixed gas line connected to the device through the product gas discharge line and further including a bypass line having one end connected to the supply line and bypassing the device having an opposite end connected between product line discharge and the mixed gas line. The mixer being arranged between bypass line and mixed gas line and the product gas discharge line and wherein the device is operable under the control of a control which is connected to a detector in the mixed gas line and controls the mixer in accordance with the enrichment of the mixed gas line.

A further object of the invention is to provide a device for the enrichment of respiratory air with oxygen which is simple in design, rugged in construction and economical to manufacture.

The various features of novelty which characterize the invention are pointed out with particularity in the claims annexed to and forming a part of this disclosure. For a better understanding of the invention, its operating advantages and specific objects obtained by its uses, reference is made to the accompanying drawings and descriptive matter in which, preferred embodiments of the invention are illustrated.

DESCRIPTION OF THE PREFERRED EMBODIMENTS

Figure 1:
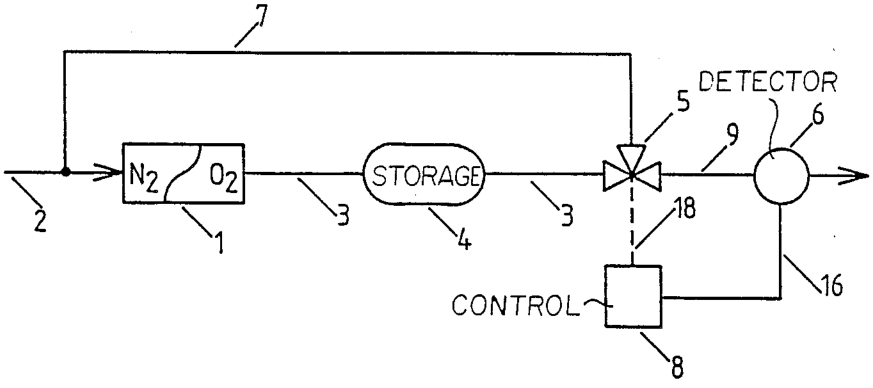
FIG. 1 is a schematic representation of a device with a single-state concentrator constructed in accordance with the invention.

Referring to the drawings in particular the invention embodied therein in FIG. 1 comprises a device for the enrichment of respiratory air which includes a gas supply line 2 and at least one adsorption device designated 1 which has a discharge into a product gas line 3 which has a storage 4 therein.

In accordance with the invention a bypass line 7 bypasses the adsorption device 1 and connects to a mixer 5 which is at a junction between the product gas line 3 and a mixed gas line 9. In accordance with the invention, a detector 6 is arranged in the mixed gas line and it is connected to a control 8 to a line 16 which acts on the mixer 5 through a line 18 to control the enrichment of the gas entering the mixed gas line 9.

In the embodiments the concentrators have pressure exchange adsorption beds serving to enrich respiratory air with oxygen. The adsorption bed 1 in FIG. 1 is supplied with supply gas by means of a supply gas line 2. It retains the nitrogen and releases oxygen into the product gas line 3. The product gas line 3 has a storage container 4, a mixing element 5 and in a following mixed gas line 9 it has an oxygen detector 6 checking the concentration of enrichment. A bypass line 7 is connected to the supply gas line 2 and to the mixing element 5. The mixing element 5 is controlled through a control unit 8. The control unit is connected through line 16 to the detector 6 and the control compares the actual value of the oxygen concentration measured by the detector 6 to an adjustable set value. The control unit 8 also controls the mixing element 5 by means of a control line 18 so that the division of product gas through the adsorption bed 1 and the division of supply gas through the bypass line 7 result in the desired oxygen concentration in the mixed gas line 9.

Figure 2:
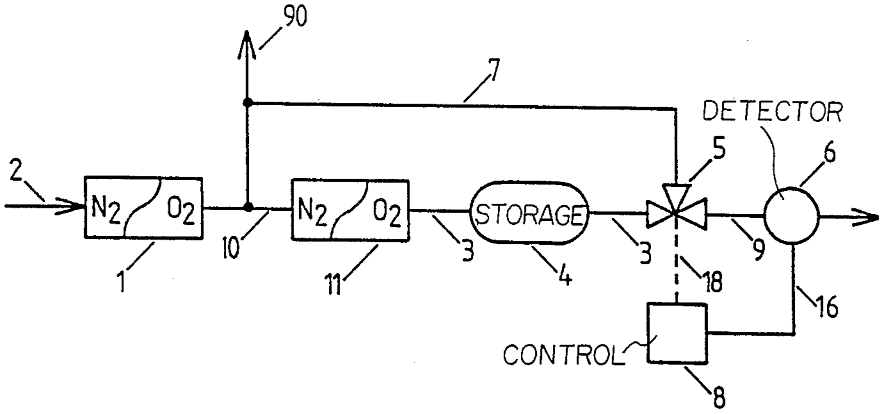
FIG. 2 is a view similar to FIG. 1 of another embodiment showing a device with a two-stage concentrator.

In FIG. 2 a two-stage device for the enrichment of the respiratory air is represented, wherein two adsorption beds 1, 11 are connected in line and are connected to one another through a connecting line 10 from which the bypass line 7 branches off. A branch line 90 for the tapping of dried supply gas branches off from said bypass line. The other design elements correspond to the ones in FIG. 1 and have the same reference numbers.

Figure 3:
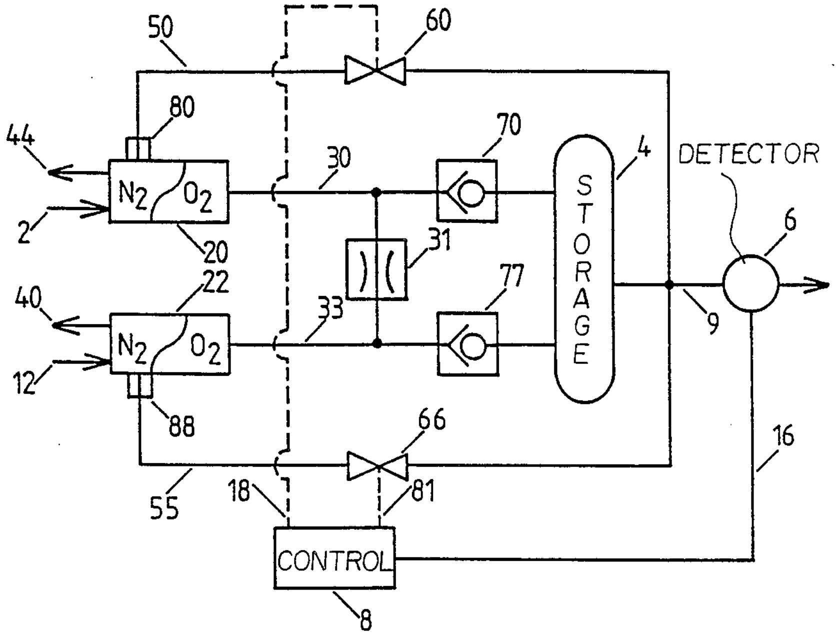
FIG. 3 is a view similar to FIG. 1 of still another embodiment showing a device with a concentrator which is actuated cyclically in an alternating fashion.

In FIG. 3 a device for the enrichment of respiratory air is represented, which comprises two adsorption beds 20 and 22 in a parallel connection and which are alternatively supplied with supply gas over respective supply gas lines 2 and 12 for the adsorption of nitrogen. While one of the adsorption beds 20 delivers a product gas enriched with oxygen, oxygen from the adsorption beds' product gas line 30 is led via a throttle element 31 through the other line 33 and through the saturated adsorption bed 22 in a counter-flow and the desorbed nitrogen is passed on to the environment by means of the venting 40. The product gas from the adsorption bed 20 is led into the storage container 4 by means of the product gas line 30 and the non-return valve 70.

The bypass line 50 starts at a tapping point 80 in the entrance area of the adsorption bed and is led into the product gas line 30 downstream of the storage container 4 by means of a controllable valve element 60. The mixture of enriched product gas from the storage container 4 and dry supply gas is supplied to a user not shown through a mixed gas line 9 having an oxygen-detector 6. The oxygen detector 6 gives a signal to the control unit 8 through the signal line 16. The control unit is connected to the respective valve elements 60 and 66 in the respective bypass lines 50 and 55 between the tapping points 80 and 88 of the adsorption beds 20, 22 by means of control lines 18, 81.

At the point when the first adsorption bed 20 is completely covered with nitrogen and therefore saturated, the previously saturated adsorption bed 22 is completely regenerated by means of the desorption with the product gas from the adsorption bed 20, so that a reverse operation of the adsorption beds 20, 22 can take place. Then the second adsorption bed 22 is supplied with supply gas from supply gas line 12 and it delivers oxygen-enriched product gas into the storage container 4 by means of its product gas line 33 and the non-return valve 77. At the same time a part of its product gas is led to the saturated adsorption bed 20 through the throttling element 31 and it is freed from the absorbed nitrogen in a counter flow, the nitrogen being passed on to the environment by the vent 44. Each valve element 60 and 66 is controlled by means of the control unit 8 so that it is closed during the regeneration phase of the respective adsorption bed and it controls the throughput portion in the respective bypass lines 50 and 55 only during the enriching phase.

While specific embodiments of the invention have been shown and described in detail to illustrate the application of the principles of the invention, it will be understood that the invention may be embodied otherwise without departing from such principles.

WHAT IS CLAIMED IS:

1. A device for the enrichment of respiratory air with oxygen, comprising a supply gas line for gas to be enriched, at least one concentrator connected to said supply gas line and having a product gas line discharge with an adjustable concentration of enrichment, means for achieving as high a concentration of enrichment as possible at an adjustable and low throughput of said concentrator including a bypass line providing a partial flow of supply gas and having an adjustment for a throughput and bypassing said product gas line and said at least one concentrator.

2. A device according to claim 1, wherein a storage container is arranged in said product gas line and is bypassed by said bypass line.

3. A device according to claim 2, wherein there are a plurality of concentrators connected in said supply line and including a connection line between said concentrators, said bypass line being connected to said connection line.

4. A device according to claim 1, wherein said at least one concentrator comprises a plurality of concentrators, said concentrators being arranged in parallel and having a throttle connecting line therebetween, said bypass line extending from each concentrator to said mixing line, said mixer comprising a valve arranged in each of said bypass line between said concentrators, each bypass line connected to said mixed gas line.

5. A device according to claim 4, further comprising a detector located in said mixed gas line and each of said concentrators having a bypass line connection with a mixer valve therein and including a control connected between each mixer valve in said mixed gas line to said detector in said mixed gas line.

6. A device according to claim 5, including a branch line provided in said bypass line.

7. A device for the enrichment of respiratory air with oxygen, comprising a gas supply line, an oxygen enrichment device in said gas supply line having a product gas line discharge, a mixed gas line connected to said product gas discharge, a bypass line connected to said supply line and bypassing said oxygen enrichment device having an opposite end connected between said oxygen enrichment device and said mixed gas line, mixer means connected between said bypass line and said mixed gas line, a detector for detecting the amount of enrichment located in said mixed line, and a control connected to said detector and to said mixer means for controlling said mixer means in accordance with the enrichment of said mixed gas line.

8. A device according to claim 7, including a storage container in said product gas line, said oxygen enrichment device comprising two oxygen enriching devices arranged one after the other in said gas supply line, said bypass line bypassing only one of said oxygen enrichment device.

9. A device according to claim 7, wherein there are at least two gas enrichment devices arranged in parallel and each connected to said gas supply line and each having a product line connected to said mixed gas line, said bypass line extending from each oxygen enrichment device to said mixed gas line, said mixer means comprising a valve in each bypass line, said control being connected between said valves in each bypass line to said detector.

10. A device according to claim 9, including a storage container interconnecting each of said oxygen enrichment devices product line and said mixed gas line, a check valve located in each oxygen enrichment device product line before said storage container, a throttle line interconnecting said product lines of each oxygen enrichment device.

* * * * *